United States Patent
Rapp et al.

(10) Patent No.: US 9,606,097 B2
(45) Date of Patent: Mar. 28, 2017

(54) PRESSURE PROBE FOR DETECTING CLATHRATES AND THE USE THEREOF

(75) Inventors: Michael Rapp, Graben-Neudorf (DE); Achim Voigt, Eggenstein-Leopoldshafen (DE); Mauro Carvalho Dos Santos, Rio de Janeiro (BR)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 546 days.

(21) Appl. No.: 14/009,500

(22) PCT Filed: Mar. 12, 2012

(86) PCT No.: PCT/EP2012/001090
§ 371 (c)(1),
(2), (4) Date: Dec. 12, 2013

(87) PCT Pub. No.: WO2012/136304
PCT Pub. Date: Oct. 11, 2012

(65) Prior Publication Data
US 2014/0090449 A1    Apr. 3, 2014

(30) Foreign Application Priority Data
Apr. 2, 2011    (DE) .......................... 10 2011 015 942

(51) Int. Cl.
*G01N 33/24*    (2006.01)
*G01N 27/22*    (2006.01)

(52) U.S. Cl.
CPC ........... *G01N 33/24* (2013.01); *G01N 27/221* (2013.01)

(58) Field of Classification Search
CPC ..................................................... G01N 33/24
(Continued)

(56) References Cited

U.S. PATENT DOCUMENTS 6,449,580 B1 * 9/2002 Bardetsky .......... G01N 33/2888
702/127
7,202,954 B2 * 4/2007 Washizu .......... G01N 33/54373
356/451
(Continued)

FOREIGN PATENT DOCUMENTS

DE    41 16 322 A1    10/1991
DE    196 44 290 A1    5/1998
(Continued)

OTHER PUBLICATIONS

Yamamuro, O. et al., "Dielectric Study of KOH-Doped Acetone and Trimethylene Oxide Clathrate Hydrates", J. Phys. Chem. Solids, vol. 54, No. 2, Feb. 1, 1993, pp. 229-235.
(Continued)

*Primary Examiner* — Michael A Lyons
*Assistant Examiner* — Hoang Nguyen
(74) *Attorney, Agent, or Firm* — FisherBroyles, LLP; Robert Kinberg

(57) ABSTRACT

A pressure probe for detecting clathrates includes a probe wall defining an inside area. A window is arranged in the probe wall. A device including a circuit board having a surface is arranged below the window. A permittivity sensor and temperature sensor are arranged on the surface of the circuit board and in thermal contact with each other and with a temperature control device. An insulating layer is disposed on the surface of the circuit board over the permittivity sensor and the temperature sensor. The window includes a part of the insulating layer.

7 Claims, 4 Drawing Sheets

(58) Field of Classification Search
USPC .......................................................... 73/53.01
See application file for complete search history.

(56) References Cited

U.S. PATENT DOCUMENTS

| | | | | |
|---|---|---|---|---|
| 7,541,004 | B2* | 6/2009 | Niksa | G01N 27/126 |
| | | | | 324/698 |
| 8,522,604 | B2* | 9/2013 | Zhe | G01M 13/02 |
| | | | | 324/204 |
| 9,176,086 | B2* | 11/2015 | Qi | G01N 27/22 |
| 2004/0250606 | A1 | 12/2004 | Buttgenbach et al. | |
| 2007/0144063 | A1* | 6/2007 | Lueking | B82Y 30/00 |
| | | | | 44/620 |

FOREIGN PATENT DOCUMENTS

| | | | |
|---|---|---|---|
| DE | 10 2006 022 290 A1 | 11/2007 | |
| DE | 10 2009 028 634 A1 | 3/2011 | |
| EP | 2 024 077 B1 | 3/2011 | |
| IT | EP2024077 | * | 2/2009 |
| JP | 6-58896 A | 3/1994 | |
| WO | 2004/109807 A2 | 12/2004 | |

OTHER PUBLICATIONS

Kliner, J. et al., "Determination of Synthetic Hydrate Content in Sand Specimens Using Dielectrics", Canadian Geotechnical Journal, vol. 43, No. 6, Jun. 1, 2006, pp. 551-562.

Park, Y., et al., "Thermal Expansivity of Tetrahydrofuran Clathrate Hydrate with Diatomic Guest Molecules", J. Phys. Chem. B, vol. xxx, No. xx, Mar. 7, 2008, pp. A-C.

Wilson, P.W., et al., "Heterogeneous Nucleation of Clathrates from Supercooled Tetrahydrofuran (THF)/Water Mixtures, and the Effect of an Added Catalyst", Chemical Engineering Science, vol. 60 (2005) pp. 2937-2941.

Sugar—Submarine Gas Hydrate Storage Locations, Partial Project A2.2, "Aktive Elektromagnetik Zur ev Aluierung und Quantifizierung von Gashydratvorkommen" [Active Electromagnetics for the Evaluation and Quantification of Gas Hydrate Deposits], BMBF Funding No. 03G0688A, Jan. 7, 2008, Ifmgeomar, Kiel, (http://www.ifm-geomarde/index.php?id=sugar_all 000).

* cited by examiner

PRESSURE PROBE FOR DETECTING CLATHRATES AND THE USE THEREOF

BACKGROUND

The invention relates to a pressure probe for detecting clathrates and the use thereof.

Inclusion compounds are referred to as clathrates (Latin: clatratus—latticed), wherein a guest molecule is enclosed inside a lattice formed by a host molecule. Naturally occurring inclusion compounds are the so-called gas hydrates, wherein gas molecules such as the methane molecules, but also carbon dioxide molecules or hydrogen sulfide molecules, are embedded as guests in a molecular lattice composed of water molecules. Inclusion compounds of methane gas in water (methane/water) are also referred to as methane hydrates or methane ice.

The forming of inclusion compounds in water or in sea water preferably occurs at high gas concentrations, at a low temperature, and with high pressure, in particular in sediments on the ocean floor where methane is formed locally as a result of the decomposition processes of bio-organic materials. Despite a specifically lower density of the gas hydrates (frequently also in the form of a sediment-gas hydrate-mixture), the adhesion to the subsurface or, specifically, heavy gas hydrate-free sediment ensures that the embedded and specifically lighter gas hydrate remains on the ocean floor. Gas hydrates were originally discovered, however, because of their capacity to clog natural gas pipelines in cold regions.

The existence of clathrates is generally detected via the acquisition of pressure/temperature and time diagrams for the respective inclusion compounds (e.g. methane/water) inside autoclaves (high-pressure measurements). Pressure/temperature diagrams, however, are frequently not precise and are subject to the typical thermo-dynamic delays. The detection with measuring technology is furthermore possible only inside a laboratory (autoclave), but not in situ or on location. No pressure/temperature diagrams furthermore exist in some cases, e.g. in the case of THF/water clathrates, since both components are liquids (see Y. Park, Y. N. Choi, S.-H. Yeon, and H. Lee, *Thermal Expansivity of Tetrahydrofuran Clathrate Hydrate with Diatomic Guest Molecules*, J. Phys. Chem. B, Vol. xxx, No. xx, XXX; P. W. Wilson, D. Lester, A. D. J. Haymet, *Heterogeneous nucleation of clathrates from supercooled tetrahydrofuran (THF)/water mixtures, and the effect of an added catalyst*, Chem. Eng. Sc. 60, 2937-41, 2005).

Clathrates in the form of liquid phases (e.g. THF/water) can be detected either optically with the aid of laser-infrared absorption or by means of viscosity measurements. However, optical testing requires special optical windows which can also be used under extreme pressure conditions, such as occur during the clathrate formation (for example 150 MPa for methane hydrate).

From the project entitled SUGAR—Submarine Gas Hydrate Storage Locations, Partial Project A2.2, "AKTIVE ELEKTROMAGNETIK ZUR EVALUIERUNG UND QUANTIFIZIERUNG VON GASHYDRATVORKOMMEN" [*Active Electromagnetics For The Evaluation And Quantification Of Gas Hydrate Deposits*], BMBF Funding No. 03G0688A, IFM-GEOMAR, Kiel, (http://www.ifm-geomar.de/index.php?id=sugar_a11000), it is known that high-frequency measurements on the ocean floor can be carried out with the aid of trailing antennas.

Japanese patent document JP 6 058 896 A discloses a device for detecting the clathrates of carbon dioxide with the aid of a conductivity sensor and a temperature sensor which are in thermal contact with a temperature control device.

German patent document DE 10 2006 022 290 A1 discloses a heater with an integrated temperature sensor on a substrate, wherein an electrically conductive thin-film layer on an insulating substructure is coated directly with an electrically conductive thin-film.

German patent document DE 10 2009 028 634 A1 describes a method for the production of a protective layer for resistance sensors, provided with a metal resistance layer, wherein the material for the protective layer is applied in such a way to the metal resistance layer that the particles of the protective layer are joined so as to form a porous protective layer.

International patent publication WO 2004/109807 A2 discloses materials that can be used for a dielectric layer on a semiconductor substrate, in particular silicon dioxide, silicon oxynitride, diamond, polymers and porous aluminum oxide.

A device is described in European patent document EP 2 024 077 B1 which can be used to record in the laboratory important parameters for the formation of clathrates, in particular the temperature, the pressure, the conductivity and the flow rate.

SUMMARY OF THE INVENTION

Starting with this premise, it is an object of the present invention to provide a pressure probe for the detection of clathrates, having the simplest possible design, which can also be used in situ or on location, for example in pipelines or on the ocean floor.

According to an embodiment, there is provided a pressure probe for detecting clathrates includes: a probe wall defining an inside area; a window arranged in the probe wall; a temperature control device; a device including a circuit board having a surface and arranged below the window; permittivity sensor and temperature sensor arranged on the surface of the circuit board and in thermal contact with each other and with the temperature control device; and an insulating layer disposed on the surface of the circuit board over the permittivity sensor and the temperature sensor, wherein the window comprises a part of the insulating layer.

According to one aspect of the invention, the pressure probe is intended to allow monitoring and predicting the imminent, especially unwanted clathrate formation in situ at critical locations, for example in oversea-installed or undersea-installed pipelines and in pumping equipment.

According to a different aspect of the invention, the pressure probe should make possible a depth exploration to prospect for natural methane hydrate deposits in undersea sediments, wherein it should simultaneously be possible to ensure the detection of the occurrence of methane hydrates in prevalent typical phases, such as in pure seawater or in a sand/sediment and seawater mixture.

Finally, according to another aspect of the invention, the pressure probe should comprise means to detect an imminent, especially unwanted, clathrate formation before it occurs in the environment.

The circuit board on which the permittivity sensor and the temperature sensor are arranged, may comprisesa typical printed circuit board material, for example a glass-fiber reinforced epoxy material, such as is generally used in the field of electronics. According to a different, alternative embodiment, a different dielectric material can also be used for the circuit board, for example, a polymer or a ceramic material.

The respective surfaces of the permittivity sensor and the temperature sensor may be coated with an insulating layer, designed to prevent the measuring of the Ohmic influences in the environment. The insulating layer functions as a chemically resistant separating layer between the sensors, including the associated electronic components, on the one hand and the outside environment on the other hand, to protect in particular against environmental influences caused by seawater, oil in pipelines and the like, thereby preventing corrosion of the metal surfaces and the connections. On the other hand, the insulating layer is permeable to electromagnetic alternating fields and radiation in the range of 10 kHz to 1GHz. The insulating layer may have a thickness between 1-1000 μm and may comprise polyurethane lacquer or parylene, which can precipitate out directly from the gaseous phase. Also suitable for use are ceramic substances, glass coatings or diamond coatings, which are mechanically more robust at the same layer thickness.

The permittivity sensor may comprise an insulated interdigital structure of a conductive electrode material. A resistance sensor may be used for the temperature sensor, in particular a PT1000, wherein a NiCrNi thermo-element or a semiconductor temperature sensor can alternatively also be used. If possible, the temperature sensor and the permittivity sensor are in good thermal contact with each other and with a temperature control device, which is preferably embodied in the form of a heating and/or cooling plate and comprises a mechanism for thermally influencing the environment to be examined of the temperature sensor, especially in cyclical variations. A heat conductor or a Peltier element may be used for the heating element while, a Peltier element or a cooling finger that is cooled from the outside may be used for the cooling element, in particular an external liquid-operated thermostat.

A device according to the invention may be installed on the inside of the pressure probe, such that it is located as close as possible underneath a window inserted into the wall (sheath) of the pressure probe, wherein the window is permeable to electromagnetic radiation in the range between 10 kHz and 1 GHz and simultaneously has the highest possible thermal conductivity. The window may be composed of suitable ceramic material, and may have a thickness from about 10 μm-1000 μm.

The window in this case may be embodied to form a part of the insulating layer that covers the surfaces of the permittivity sensor and the temperature sensor.

One embodiment provides that the electronic control is installed in the wall of the pressure probe, in particular the electronic control for the permittivity sensor, the temperature sensor, and the temperature control device.

The pressure probe according to the invention can be used in conjunction with a method for determining the phase-transition temperature from starting solutions to clathrates by measuring the dielectric properties of a substance mixture with the permittivity sensor, with an applied high-frequency signal, and simultaneously measuring the temperature with an external temperature setting.

Whereas pure water (e.g. bi-distilled water) has an extremely high permittivity of approximately 80, clathrates and water ice have a permittivity below 10. As a result, pure water on the one hand can be distinguished from clathrates and water ice on the other hand. Clathrates can furthermore be detected individually if the formed clathrates have different crystallization phases with respectively different dielectric constants.

The pressure probe according to the invention is therefore suitable for analyzing the forming of clathrates from the starting solutions. Modified conditions for the formation can furthermore also be analyzed by influencing, especially suppressing, preventing, or catalyzing the clathrate formation with the aid of additives.

The pressure probe according to the invention is furthermore suitable for use with a method for the stationary monitoring and predicting of the clathrate formation, using the following method steps:

Holding the temperature of the pressure probe to below the environmental temperature with the aid of a cooling element, integrated into the pressure probe, but above the melting point for the pure watery phase and/or the dew point for the pure moisture of natural gases in a pipeline; and Triggering a signal as soon as individual clathrates form on the pressure probe, the existence of which is detected.

An (alarm) signal can thus already be triggered before a phase conversion to clathrates occurs in the general environment of the pressure probe.

The pressure probe according to the invention is therefore suitable for the (alarm) monitoring and for predicting an imminent and in particular undesirable clathrate formation in situ at critical locations, for example in oversea-installed and undersea-installed pipelines and in pumping equipment. In the event that an alarm is triggered, the environment around the pressure probe could be changed (heated), following a calibration of the operating parameters, so that the imminent formation of clathrates may be suppressed or prevented.

Finally, the pressure probe according to the invention is suitable to be used with a method for mobile depth sounding, in particular for the three-dimensional prospecting for natural methane gas deposits, using the method steps:

Cyclical changing of the temperature of the pressure probe via the environmental temperature, with the aid of a heating element that is integrated into the pressure probe, thereby also cyclically melting any existing methane ice in the environment and/or on the surface of the pressure probe and causing a jump in the permittivity of approximately 80 because of the briefly generated water film on the surface of the pressure probe, starting with typical values of 6-10 for the icing.

The existence of clathrates/water ice can thus be detected on the one hand and the existence of water only on the other hand, independent of the respective sand and sediment content. If either water ice or clathrates are present in the environment, immediately surrounding the pressure probe, the forming of water in the described temperature cycle will also cause a cyclical change in the permittivity, even if silt and sediments are present. However, the presence of clathrates can be detected unambiguously since water ice cannot exist in typical undersea sediments according to fundamental considerations, in that the temperature is above 4° C. and the density is too high on the ocean floor. This is additionally supported by the condition that the temperature of the pressure probe must be above the melting point of the watery phase.

The pressure probe according to the invention can therefore be used for mobile depth sounding with the aid of a pressure probe, for the three-dimensional prospecting for natural methane gas deposits in sediments on the ocean floor or in sufficiently deep bodies of water, in particular starting at a depth of 400 m. For this, the sensor makes it possible to distinguish between the four typical environmental states on or in the ocean floor:

seawater;
mixture of sand/sediment and seawater;
methane hydrate and mixture of sand/sediment and methane hydrate in seawater.

BRIEF DESCRIPTION OF THE DRAWINGS

The invention is explained in the following in further detail, with the aid of exemplary embodiments and the Figures, which show in.

DETAILED DESCRIPTION

Figure 1:
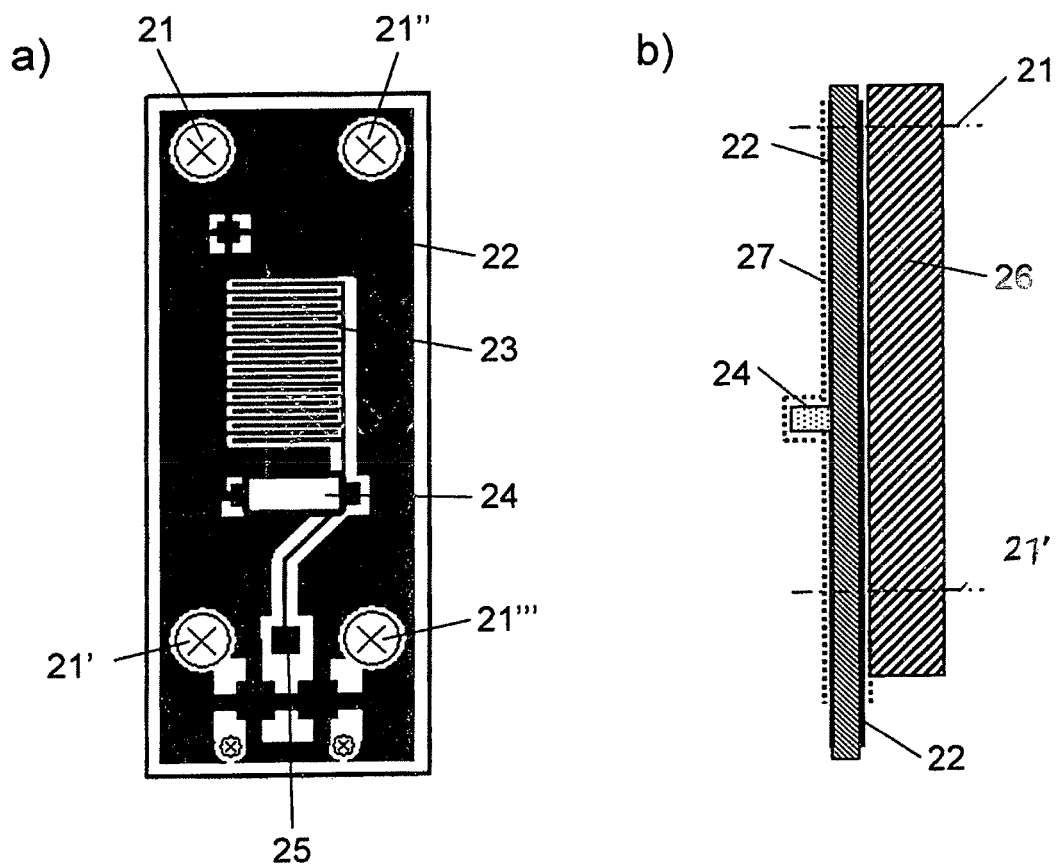
FIG. 1 A schematic representation of the device according to the invention in (a) a view from above and/or (b) a view from the side.

FIG. 1 shows in (a) a view from above and/or in (b) a view from the side of a schematically drawn device 20 for the detection of clathrates. A permittivity sensor 23, for example consisting of an interdigital structure of conductive electrode material that is insulated with parylene, may be affixed to a glass-fiber reinforced epoxy circuit board (printed circuit board) 22. The interdigital structure, which is affixed insulated, may function to determine the permittivity values (dielectric conductivity) in the area surrounding the permittivity sensor 23, at a frequency range of 10 kHz up to 1 GHz. The circuit board 22 furthermore may contain a temperature sensor 24, preferably a PT 1000, for detecting the temperature in the environment to be analyzed.

The permittivity sensor 23 and the temperature sensor 24 may be in good thermal contact with each other as well as with a preferably plate-shaped temperature control device 26 which could be used to influence the environment to be measured around the permittivity sensor 23 and the temperature sensor 24. The temperature control device 26, which in this case may be connected via assembly bores 21, 21' 21", 21''' to the circuit board 22, may comprise a copper surface that could be heated and cooled and may function as an electrical heating as well as a cooling element, to be activated thermally via the inside-arranged liquid channels and a Haake thermostat.

The surface of the device, including the temperature sensor 24 and the permittivity sensor 23 with the interdigital electrodes, may be provided with an electrically insulating and chemically resistant layer 27 of a protective lacquer coating used for circuit boards, having a thickness ranging from 1-100 μm.

Figure 2:
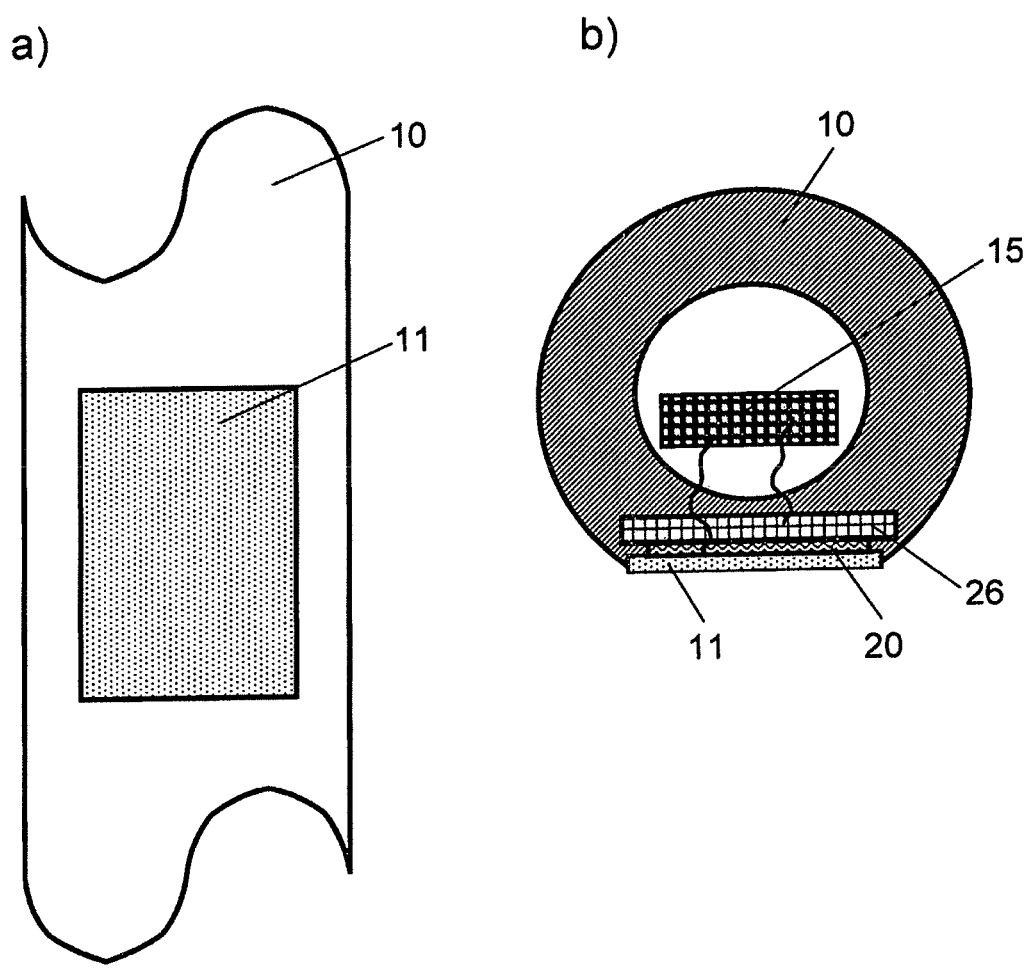
FIG. 2 A schematic representation of the pressure probe with therein integrated device according to the invention, in (a) a view from above and/or (b) a view from the side.

FIG. 2 schematically illustrates a pressure probe 10, in a view from above (a) and/or in a cross-sectional view (b), for which the inventive device 20 may be integrated at a flattened location directly behind a window 11. The permittivity sensor 23 and the temperature sensor 24 may make good thermal contact with the preferably plate-shaped temperature control device 26 (thermostatting). The electronic control 15 may be installed within the pressure probe 10. The window 11 has a thickness ranging from 10-100 μm and may comprise an electrically insulating material, preferably a stable ceramic material, which simultaneously functions as insulating layer 27.

FIGS. 3 to 6 show the results of exemplary tests carried out with the water/water ice system and/or the water/water ice and sand system. For this purpose, the device was submerged into a vessel having a volume of 100 ml and filled with bi-distilled water. The vessel was accommodated completely inside a thermally insulated container filled with tap water and ice cubes, designed to create measuring conditions around the freezing point for water (0° C.).

Figure 3:
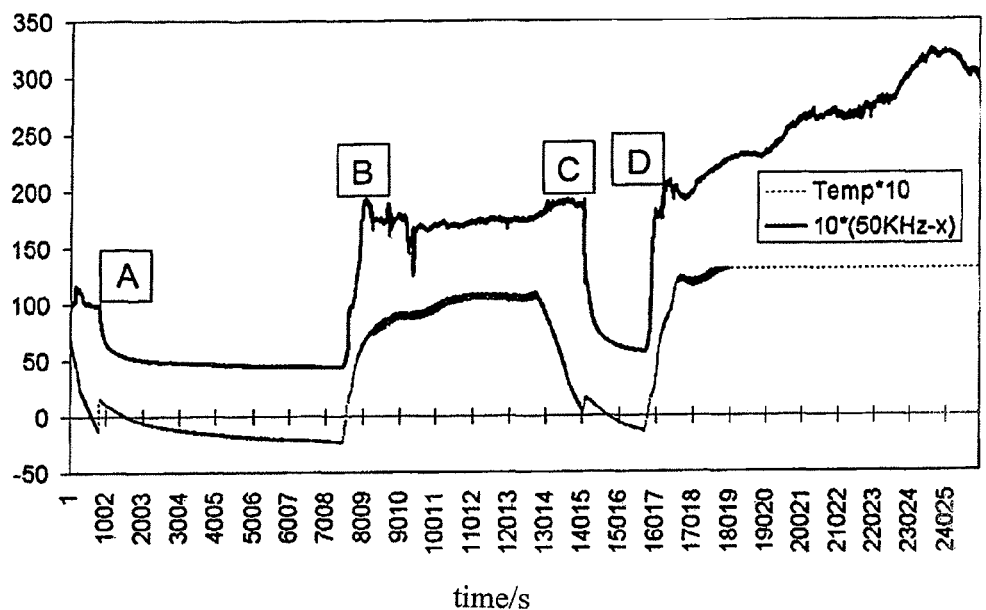
FIG. 3 A graph showing tests carried out with bi-distilled water during a twice freezing over and respectively following thawing.

FIG. 3 illustrates tests carried out with bi-distilled water and twice freezing over [A], [C] and respectively the following thawing [B], [D], wherein the start is just prior to the first freezing over [A]. A spike or overshooting can be seen at 1140s, which indicates a delayed freezing over and/or a latent heat. Starting at the point of the actual freezing over, meaning temporally after the peak caused by the latent heat, the permittivity sensor 23 shows a slow falling off to higher oscillation frequencies (shown as signal decay through difference forming in FIG. 3), wherein this leads to a lowering of the permittivity values.

Figure 4:
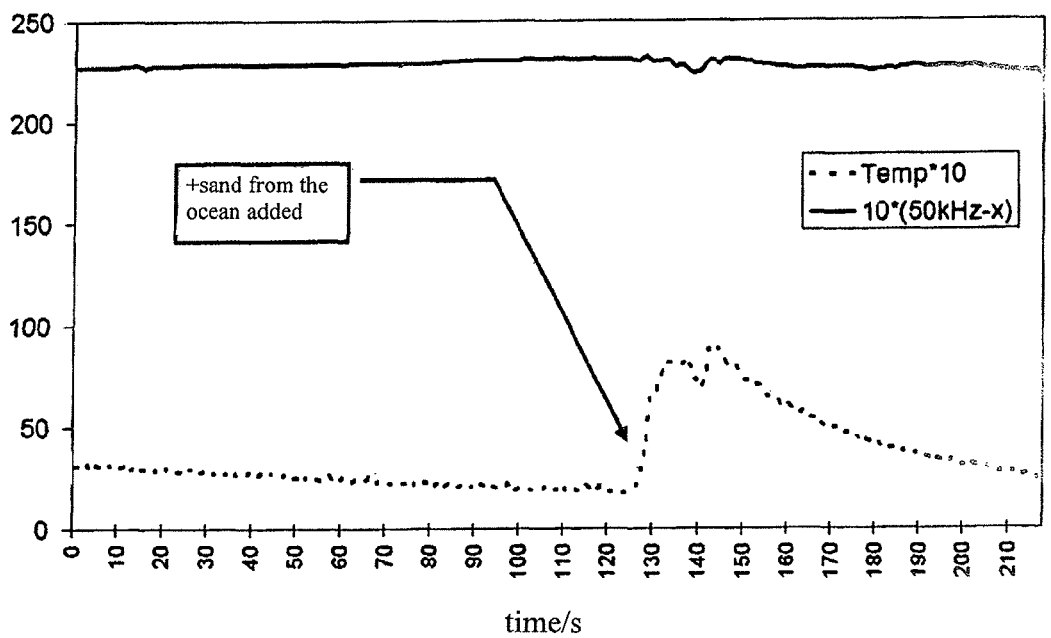
FIG. 4 A graph showing tests carried out during the filling in of sand.

The action of adding the sand is shown in FIG. 4. The increased temperature of the sand caused a deflection of the temperature sensor 24 toward higher temperatures while the permittivity sensor 23 shows practically no change at all. On the one hand, this is due to its exclusive sensitivity on the surface and, on the other hand, is caused by the fact that the water has the high permittivity and that not enough water is displaced on the surface of the sensor to cause a significant change.

Figure 5:
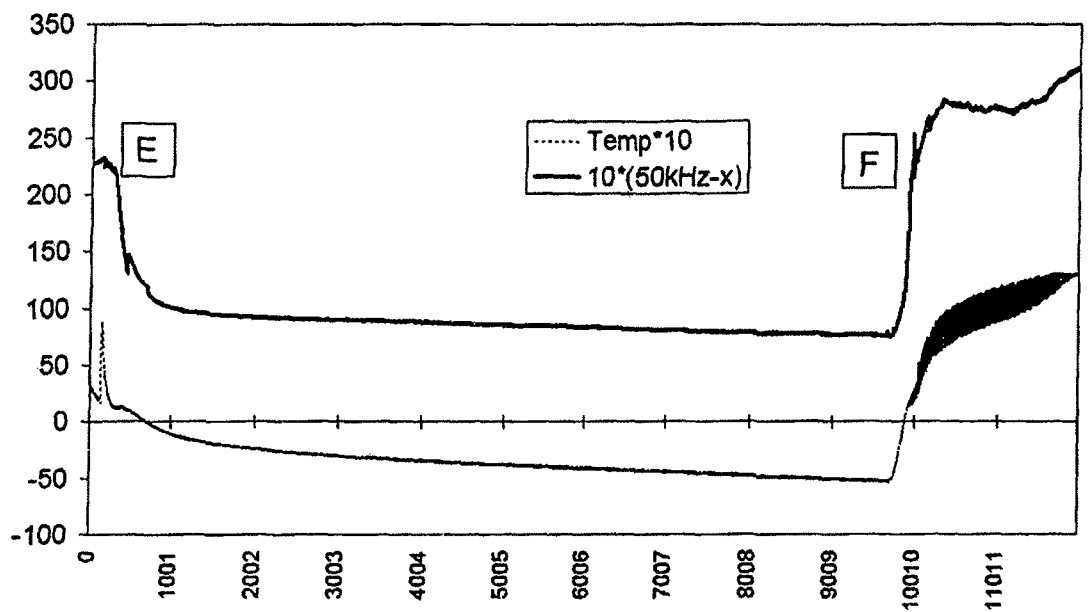
FIG. 5 A graph showing tests carried out during the freezing over of a sand/water mixture.

FIG. 5 shows the freezing over [E] and the subsequent thawing [F] of a sand/water mixture (silt) which can be followed easily by viewing the course of the temperature sensor 24. A forming of latent heat cannot be detected in this case, which is presumably due to the large surfaces of the available sand grains which offer the water a sufficient number of nuclei for a spontaneous freezing over. The permittivity sensor 23 shows higher frequencies, as expected, during the freezing over [E] of the mixture, wherein this is shown in FIG. 5 as signal decay owing to the difference forming.

Figure 6:
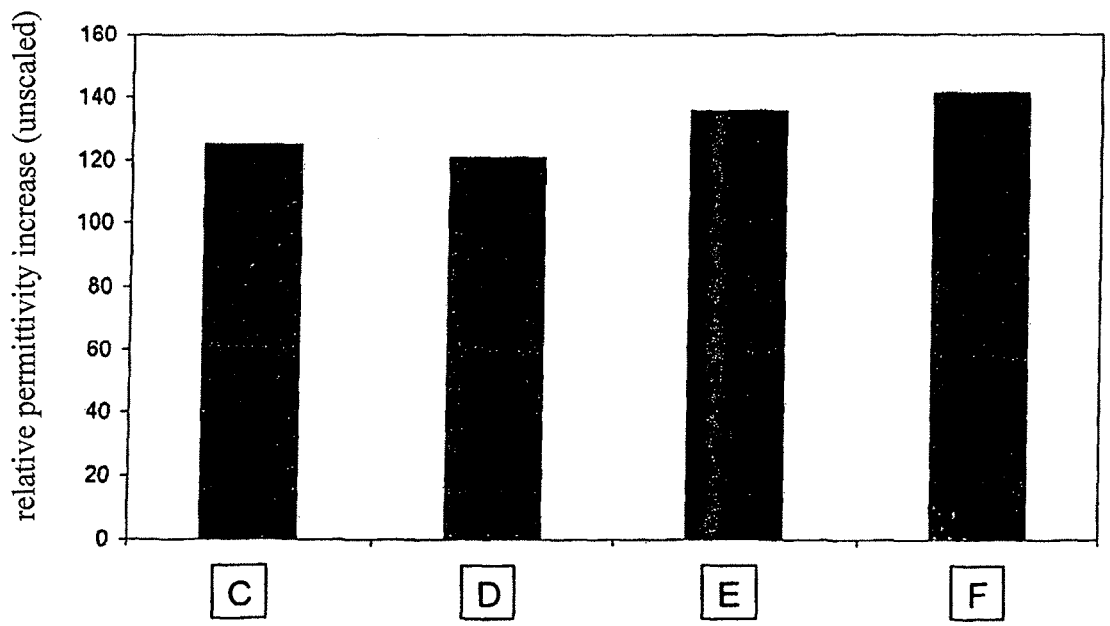
FIG. 6 A bar chart showing permittivity increase as the respective consequence of various aforementioned actions.

In FIG. 6, the respective permittivity increase is summarized and is shown as the result of the aforementioned actions [C] to [F]. In contrast to a conductivity sensor (not shown herein), it is quite obvious that the signal from the permittivity sensor 23 reacts with high sensitivity to a freezing over and/or to clathrates, but is not sensitive to the difference between water and a water/sand mixture. The detection of water ice/clathrates is therefore unambiguous when using the combination of permittivity sensor 23 and temperature sensor 24. The unambiguous proof of the existence of clathrates and not of water ice in the final analysis is based on the aforementioned consideration that no water ice can exist in typical sediments on the ocean floor or in deep bodies of water.

The invention claimed is:

1. A pressure probe for detecting clathrates, comprising:
   a probe wall defining an inside area;
   a window arranged in the probe wall;
   a temperature control device adapted for cyclically changing the temperature of the probe;
   a device including a circuit board having a surface and arranged below the window;

a permittivity sensor and temperature sensor arranged on the surface of the circuit board and in thermal contact with each other and with the temperature control device; and an insulating layer disposed on the surface of the circuit board over the permittivity sensor and the temperature sensor, wherein the window comprises a part of the insulating layer and is simultaneously permeable to electromagnetic radiation in a range between 10 kHz and 1 GHz and is thermally conductive.

2. The pressure probe according to claim 1, wherein the permittivity sensor includes an insulated interdigital structure comprising a conductive electrode material.

3. The pressure probe according to claim 1, wherein the temperature control device comprises a heating and/or cooling plate.

4. The pressure probe according to claim 1, wherein the insulating layer comprises one of a polyurethane lacquer, parylene, glass, a ceramic material, or a diamond film.

5. The pressure probe according to claim 1, further comprising an electronic control located in the inside area defined by the probe wall.

6. A method for monitoring, predicting, and suppressing the imminent formation of clathrates, comprising utilizing the pressure probe according to claim 1.

7. A method for prospecting for natural methane hydrate deposits in sediments on the ocean floor or in bodies of water, comprising utilizing the pressure probe according to claim 1.

* * * * *